United States Patent [19]
Reiss

[11] Patent Number: 5,549,656
[45] Date of Patent: Aug. 27, 1996

[54] COMBINATION NEUROMUSCULAR STIMULATOR AND ELECTROMYOGRAPH SYSTEM

[75] Inventor: Hans W. Reiss, Encinitas, Calif.

[73] Assignee: Med Serve Group, Inc., Encinitas, Calif.

[21] Appl. No.: 441,063

[22] Filed: May 15, 1995

Related U.S. Application Data

[63] Continuation of Ser. No. 106,718, Aug. 16, 1993, abandoned.

[51] Int. Cl.⁶ .......................... A61N 1/32; A61B 5/0488
[52] U.S. Cl. .................. 607/48; 607/63; 607/67; 607/70; 128/733
[58] Field of Search .................. 607/48, 49, 62, 607/63, 70, 72, 74, 67, 148, 152; 128/733, 905

[56] References Cited

U.S. PATENT DOCUMENTS

| | | | |
|---|---|---|---|
| 4,582,049 | 4/1986 | Ylvisaker | 607/62 X |
| 4,976,264 | 12/1990 | Petrofsky | 607/48 |
| 5,070,873 | 12/1991 | Graupe et al. | 607/48 |
| 5,092,329 | 3/1992 | Graupe et al. | 607/49 X |
| 5,133,354 | 7/1992 | Kallok | 607/48 |
| 5,300,096 | 4/1994 | Hall et al. | 607/48 |

FOREIGN PATENT DOCUMENTS 2941991  4/1980  Germany .............................. 128/733

OTHER PUBLICATIONS

"Use of ramp threshold feedback for learning of fine muscular control," Medical & Biological Engineering & Computing, No. 2 Mar., 1979, pp. 268–270.
"Electrogram," Electronics Today International, Mar. 1980, vol. 9, No. 3 pp. 56–61.

*Primary Examiner*—William E. Kamm
*Assistant Examiner*—Jeffrey R. Jastrzab
*Attorney, Agent, or Firm*—John R. Duncan; Frank D. Gilliam

[57] ABSTRACT

A combined dual channel electromuscular stimulator for directing electrical pulses into the skin and a dual channel electromyograph for detecting electrical signals generated in muscles. The electromuscular stimulator includes electronic circuitry for generating electrical pulses, controlling the pulse rate and intensity and controlling various pulse characteristics. The pulses are administered by skin contacting electrodes. The electromyograph includes skin contacting electrodes for receiving input signals from the skin and electronic circuitry for receiving detected signals without interference with the stimulator output signals, amplifying, filtering and displaying the input signals. A control panel includes switches and controls for varying the various system parameters.

14 Claims, 5 Drawing Sheets

COMBINATION NEUROMUSCULAR STIMULATOR AND ELECTROMYOGRAPH SYSTEM

This is a continuation of application 08/106,718 filed on Aug. 16, 1993, now abandoned

BACKGROUND OF THE INVENTION

This invention relates in general to electrotherapy apparatus and, more specifically, to a device that combines a neuromuscular stimulator for electrically stimulating muscles and an electromyograph for measuring the stimulation and its affects.

A wide variety of devices have been developed for applying a low intensity direct alternating current to the skin to stimulate muscles or nerves, to relieve pain, etc. Typical of these are the nerve stimulation devices described by Hudleson et al. in U.S. Pat. No. 4,232,680, Takeuchi et al. in U.S. Pat. 4,895,153 and Kenyon et al. in U.S. Pat. No. 4,723,552. Electrical energy has also been introduced into the skin to relieve sinus and nasal congestion as described by Claude et al. in U.S. Pat. No. 4,926,880 and to treat skin ulcers, infections and the like as described by Ellis in U.S. Pat. No. 4,019,510. Means have been provided to measure resistance of skin areas to determine those most susceptible to treatment by light electrical or magnetic energy, as described by Tomecek in U.S. Pat. No. 4,112,923.

The prior devices administer electrical energy at a variety of frequencies and in different patterns. Typical of these is the system disclosed by Rossen in U.S. Pat. No. 4,989,605 which applies a carrier signal to the skin through an electrode. The signal is in the form of D.C. bursts in the frequency range of 10,000 to 19,000 Hz which is modulated on and off at a lower frequency. Other typical devices include the microprocessor controlled device for applying a low frequency pulse train and a modulated high frequency pulse train to a patient through an electrode as disclosed by Padjen et al in U.S. Pat. No. 4,719,922, a device in which a constant current square wave signal is directed into the body between two electrodes as described by Hudleson et al in U.S. Pat. 4,232,680 and a device in which a high frequency low amperage current is applied to a body through an electrode as described by Liss et al in U.S. Pat. 3,902,502.

These prior art devices, although effective to an extent, generally simply provide treatment and later evaluate the effectiveness of the treatment subjectively, through lower perceived pain or physiological changes measured in muscles or nerves. In order to obtain optimum application of electrical energy and optimum results, the results of the stimulation should be measured concurrent with the treatment. Thus, there is a continuing need for devices that measure effectiveness during treatment, so that the treatment intensity, duration, location, etc. can be varied as necessary for optimum results.

SUMMARY OF THE INVENTION

The above noted problems, and others, are overcome in accordance with this invention by a device which combines a dual channel electromuscular stimulator (EMS) and a dual channel electromyograph (EMG). Separate input and combined threshold controls, display and audio outputs are provided, with a circuit that allows simultaneous, synergistic, operation without interference. A filtering section is provided in the EMG circuitry that rejects frequencies below about 100 Hz while the maximum frequency of the EMS is about 80 Hz.

The EMS section basically includes electronic circuit elements for controlling the output pulse rate and intensity, for controlling on and off times of the output pulse, for providing a "soft" start for the output pulse, for alternating the two outputs and for controlling output parameters.

The EMG section basically includes a protection circuit that acts to reject the EMS signal (both signals being applied to the inputs) so that the EMG signals are all above 100 Hz and the EMS signals are all below about 80 Hz, dual high impedance input circuits, dual amplifiers and circuit elements for limiting the frequency range of the amplified signals to eliminate unwanted signals and noise, for controlling the signal detection threshold, for controlling the amplification ranges and for displaying the intensity of the input signal, which may include an audible device for indicating input signal intensity.

BRIEF DESCRIPTION OF THE DRAWING

Details of the invention, and of certain preferred embodiments thereof, will be further understood upon reference to the drawing, wherein.

DETAILED DESCRIPTION OF PREFERRED EMBODIMENTS

Figure 1:
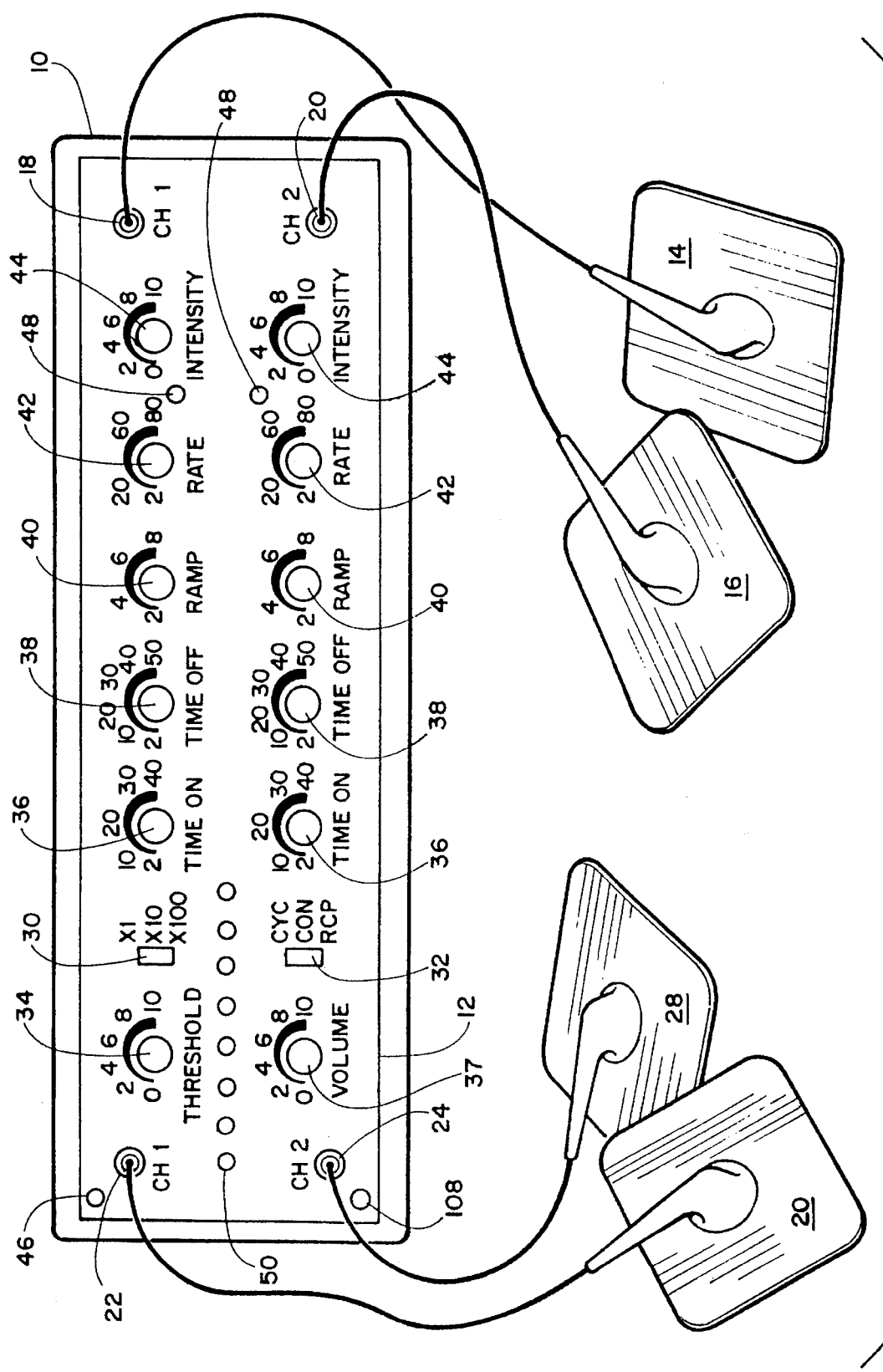
FIG. 1 is a front elevation view of the cabinet containing the circuit components, batteries, etc.

The overall system of this invention is housed in a box-like housing 10 as seen in front elevation in FIG. 1. Housing 10 contains the circuit components as described below, batteries, etc. Various control knobs, jacks, etc are provided on the front panel 12 of housing 10. Two electrode pads 14 and 16 are connected to channel 1 and channel 2 output jacks 18 and 20, respectively, from the EMS section. At the opposite end of panel 12, input jacks 22 and 24 for channel 1 and channel 2 of the EMG section are provided, into which electrode pads 26 and 28, respectively, are plugged. Any electrode pads of the sort used for EMG pickup may be used. Preferably, the pads have small contact areas to eliminate large capacitance between contacts. Typical of such pads are those described in my copending U.S. patent application, Ser. No. 07/953,945, filed Sep. 9, 1992 now U.S. Pat. No. 5,324,317

The controls for all of the variable parameters of the EMS and EMG circuits may be provided on the front of panel 12. Besides the controls and jacks shown, a conventional battery elimination power connection may be provided, if desired, so that outside power may be used in place of, or in addition to, internal battery power. Also, any desired output jacks may be provided, such as to direct an audible EMG signal to headphones, a remote control or the like. Slide switch 30 is provided for varying sensitivity by factors of 10 or 100. Another slide switch 32 provides selection of any one of cycled (CYC), constant (CON) and reciprocal (RCP) positions.

As detailed below, in the constant position only the intensity and rate controls operate and both channels operate independently.

In the cycled position the time on, time off, ramp, rate and intensity controls are operational. The time on control determines the on time of the output pulses from typically about 1 second to about 60 seconds. The time off contact determines the off time of the pulses from typically about 1 second to about 60 seconds. These controls together form a time controlled period of on and off for the output pulses with each channel operating independently. The ramp control controls the time for the output pulse to go to full output voltage and is adjustable, typically, from 0 to about 8 seconds.

In the reciprocal position the individual channel controls all operate but when one channel is on the other is off. Depending on channel control settings, the two channel outputs will alternate at a rate of up to a maximum of about once each 20 seconds.

A threshold control 34 is provided to set the signal detection threshold in the EMG section. A volume control 37 sets the volume of an audible signal indicating the input from the EMG detectors. Pairs of knobs 36 and 38 set the length of time the output pulse is "on" and "off", respectively, in the EMS section for each channel. The rate at which the output signal ramps up to full signal strength at the start of each pulse cycle is set by knobs 40. Knobs 42 control rate; controlling the output pulse from about 2 pulse/sec. to about 80 pulses/sec. Knobs 44 control intensity typically from about 0 to 60 volt maximum. A light emitting diode 46 is provided which is adapted to glow in the event that the batteries are low. Light emitting diodes 48 are connected to give a visual indication of the output pulse by flashing when the output pulse is on. A series of light emitting diodes 50, four green, one yellow and three red, is provided to indicate the applied voltage. The LED display provides a relative indication of the amount of signal detected by the EMG. In use, the threshold and range switches are adjusted so that all of the green LED's light and the yellow LED just lights when the selected muscle contracts as desired. The red LED's indicate contractions of the muscle at a rate beyond the rate recommended by the therapist.

Figure 2A:
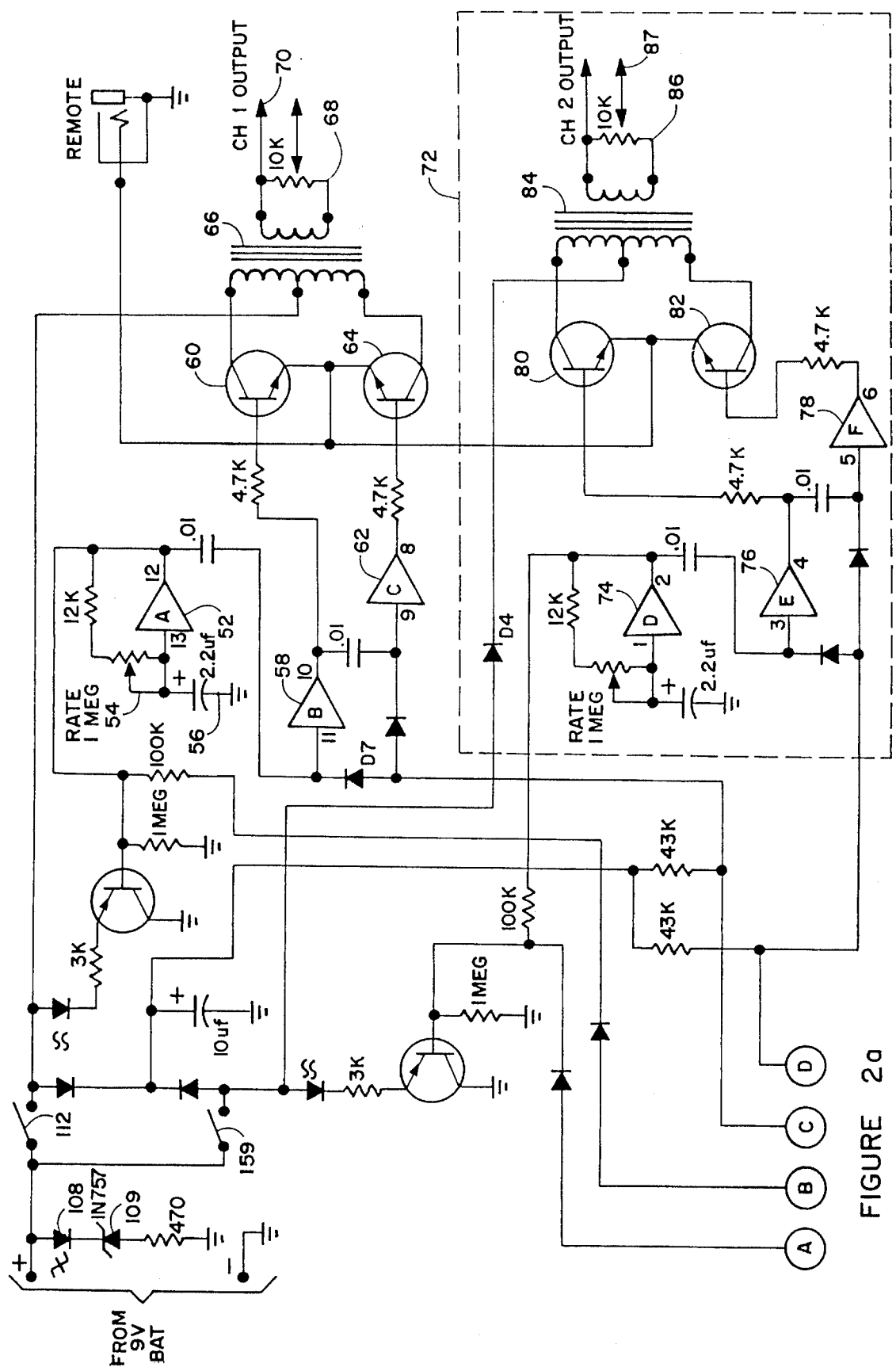
FIG. 2a and 2b are schematic circuit diagrams showing interconnected portions of the EMS circuit section.
Figure 2B:
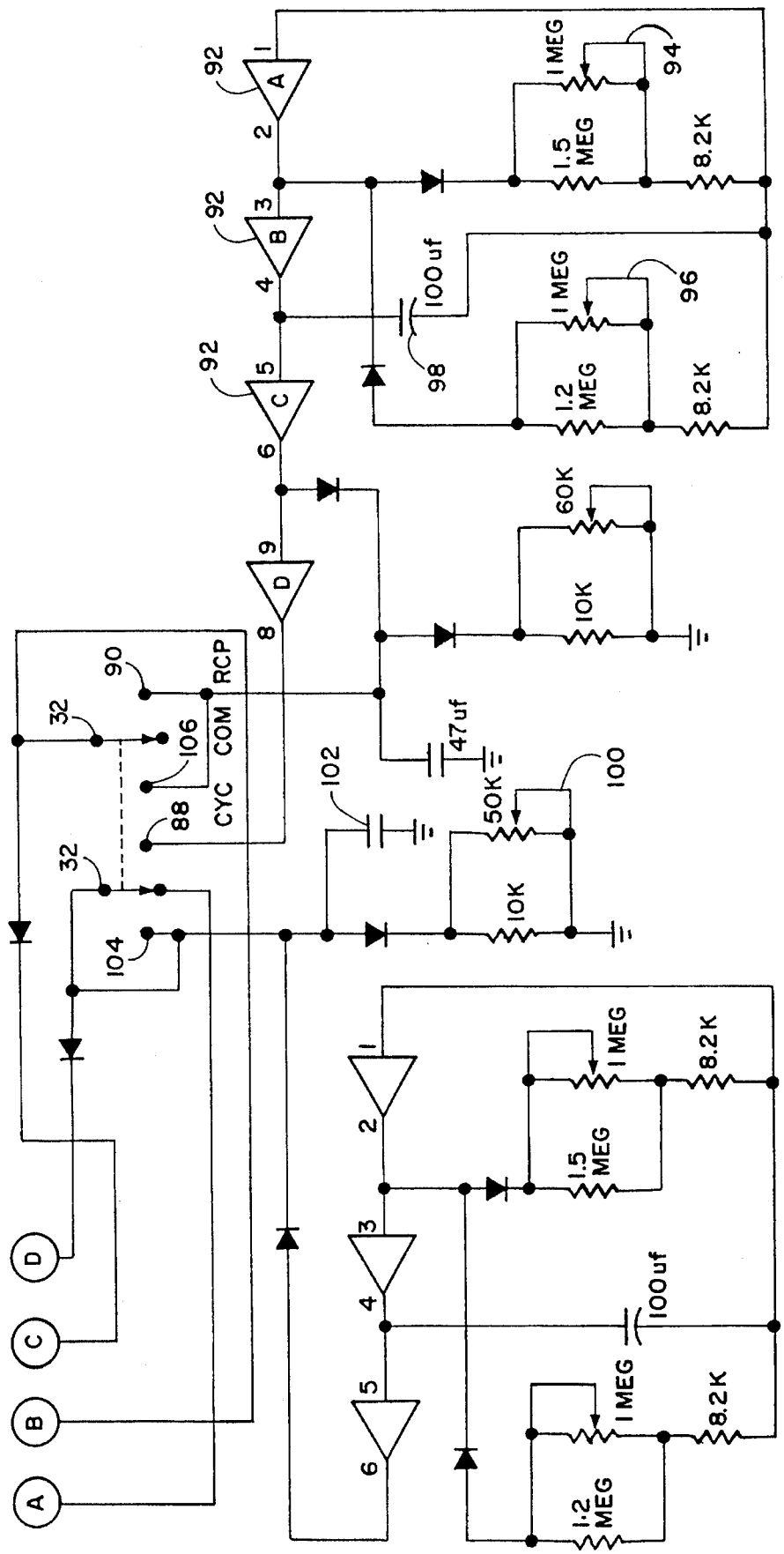

Details of a preferred electronic circuit for the electromuscular stimulator (EMS) are provided in FIGS. 2a and 2b, broken for purposes of illustration at connection points A—A, B—B and C—C. The EMS circuit includes components for controlling the output pulse rate and intensity, for controlling the on and off times of the output pulse, for providing soft start for the output pulse, for alternating the two outputs and for controlling various output parameters.

An RC type oscillator 52 (section A of the first integrated circuit, typically a 4584 available from Motorola) with a variable resistor 54 and a fixed capacitor 56 provides pulse generation and frequency control over a typical range of from about 2 Hz to about 80 Hz (under control of knob 42 as seen in FIG. 1). The output of oscillator 52 is connected to the input of buffer/invertor 58 (section B of the first IC) and the input of transistor 60, which is one half of a push/pull output stage. The inverted output 62 from section C of the first IC is connected to the input of transistor 64, forming the second half of the push/pull output stage.

The push/pull output stage is connected to the input of transformer 66. The output of transformer 66 is connected to output intensity control 68 (controlled by knob 44 in FIG. 1) and from there to the output jack 70 for the first channel. Output intensity is typically controlled over a range of about 0 volts to 60 volts, with an output current of about 0 mA to 98 mA. Output wave form is preferably an asymmetric bi-phasic rectangular pulse.

The second channel operates in the same manner as the first channel and is outlined by broken line 72. The three sections of an integrated circuit, a 4584 as above, correspond to sections 52, 58 and 62, respectively, as described above. Transistors 80 and 82 provide a push/pull output stage, corresponding to transistors 60 and 64, respectively, as described above. Transformer 84, intensity control 86 and output jack 87 correspond to transformer 66, intensity control 68 and output jack 70, described above.

The output of the EMS is controlled and modified by cycled/constant/reciprocal switch 32, seen in FIG. 1 typically as a slide switch, and shown in FIG. 2b as ganged pair of switches 32. With the switch 32 in the "constant" position, as shown in FIG. 2b, only the intensity and rate controls operate and each channel operates independently. In the "cycled" position, with switches 32 in the right-most position, closing a circuit to contacts 88 and 90, an integrated circuit 92 (typically a 4584) made up of sections 92a–92d combined with variable resistors 94 and 96 and capacitor 98 control the time on and time off periods of the output by controlling the charge and discharge times of capacitor 98 by varying resistors 94 and 96, under the control of knobs 38 (FIG. 1). The "on" time can typically be controlled from about 1 to 60 seconds and the off time can typically be controlled from about 1 to 60 seconds.

The output of the on and off time control circuit is connected to the ramp control circuit made up of variable resistor 100 and capacitor 102 via contact 88 and line 104 when switches 32 are in the left-most position. The variable charging time of capacitor 102 allows a slow or soft turn on of the output pulse over a time of from about 2 to 8 seconds, under the control of knob 40 (FIG. 1). The output of the on and off circuit, the ramp circuit and the time on and off circuit is connected to the input of IC sections 58 (first channel) and/or 76 (second channel) where it is mixed with the output of the oscillator (rate) circuits to control the output of the device at output jacks 70 and 87.

In an alternative operation mode, with the switch in the reciprocal position, the outputs of sections 92c and 92d are applied to the inputs of IC sections 58 and 76. As these outputs are of opposite polarity, one channel will operate while the other is off with the timing controlled by the on/off settings of IC 92.

In the reciprocal position of switch 32 (the right most position in FIG. 2b), closing the circuit to contacts 88 and 90, the output of the two channels will alternately turn on and off about every 20 seconds. The individual channel controls all operate but when one channel is on the other is off. Depending on channel control settings the channel 1 and 2 outputs will alternate at a selected rate of up to about 20 seconds.

A light emitting diode 108 and diode 109 are provided on the power line to show that the battery has sufficient charge.

Either of the two EMS sections can be independently turned on or off by one of the switches 112 and 159. Also, a remote control jack 114 may be provided for control of the output without turning the unit off.

Figure 3A:
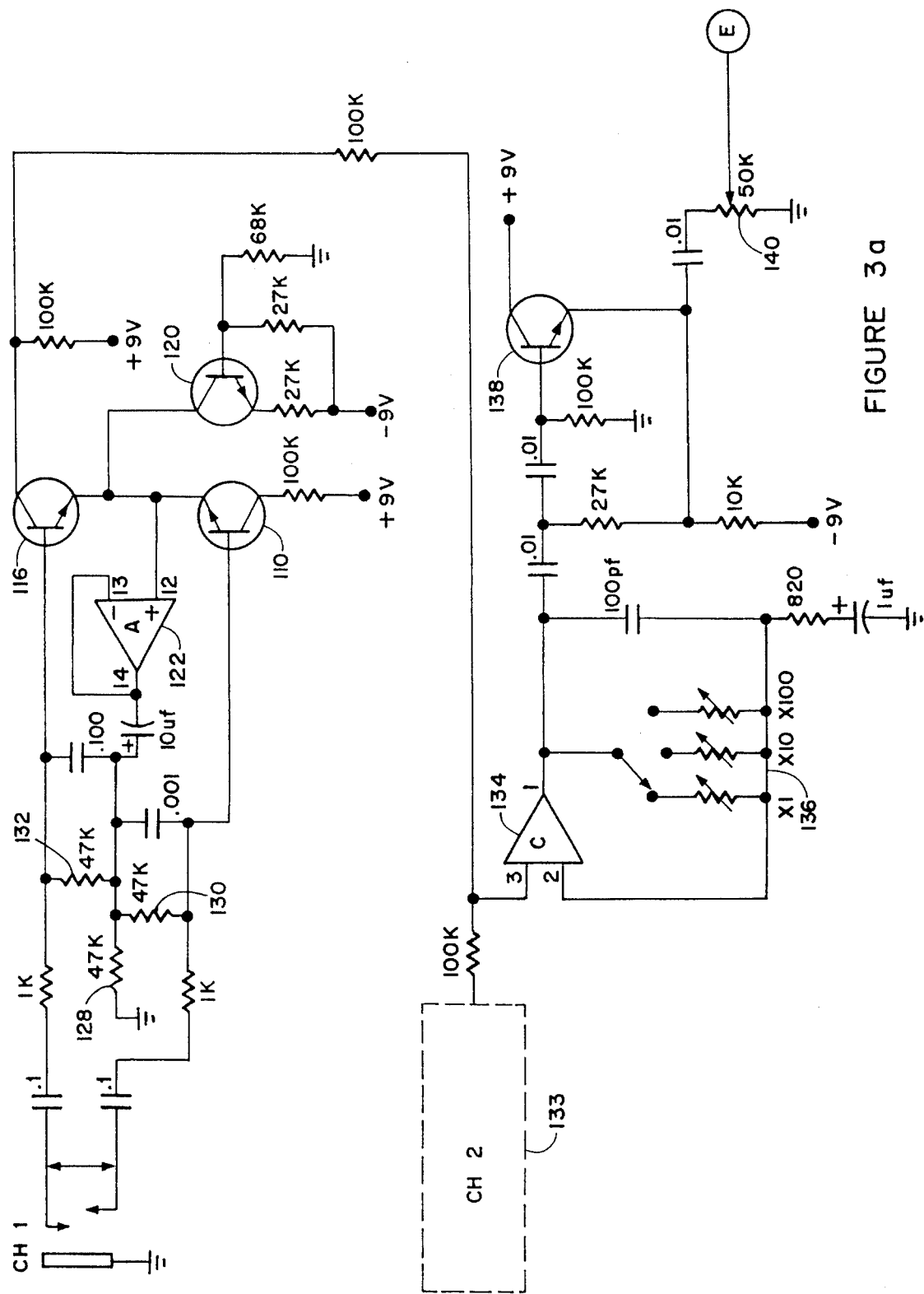
FIG. 3a–3c are schematic circuit diagrams showing interconnected portions of the EMG circuit section.
Figures 3B, 3C:
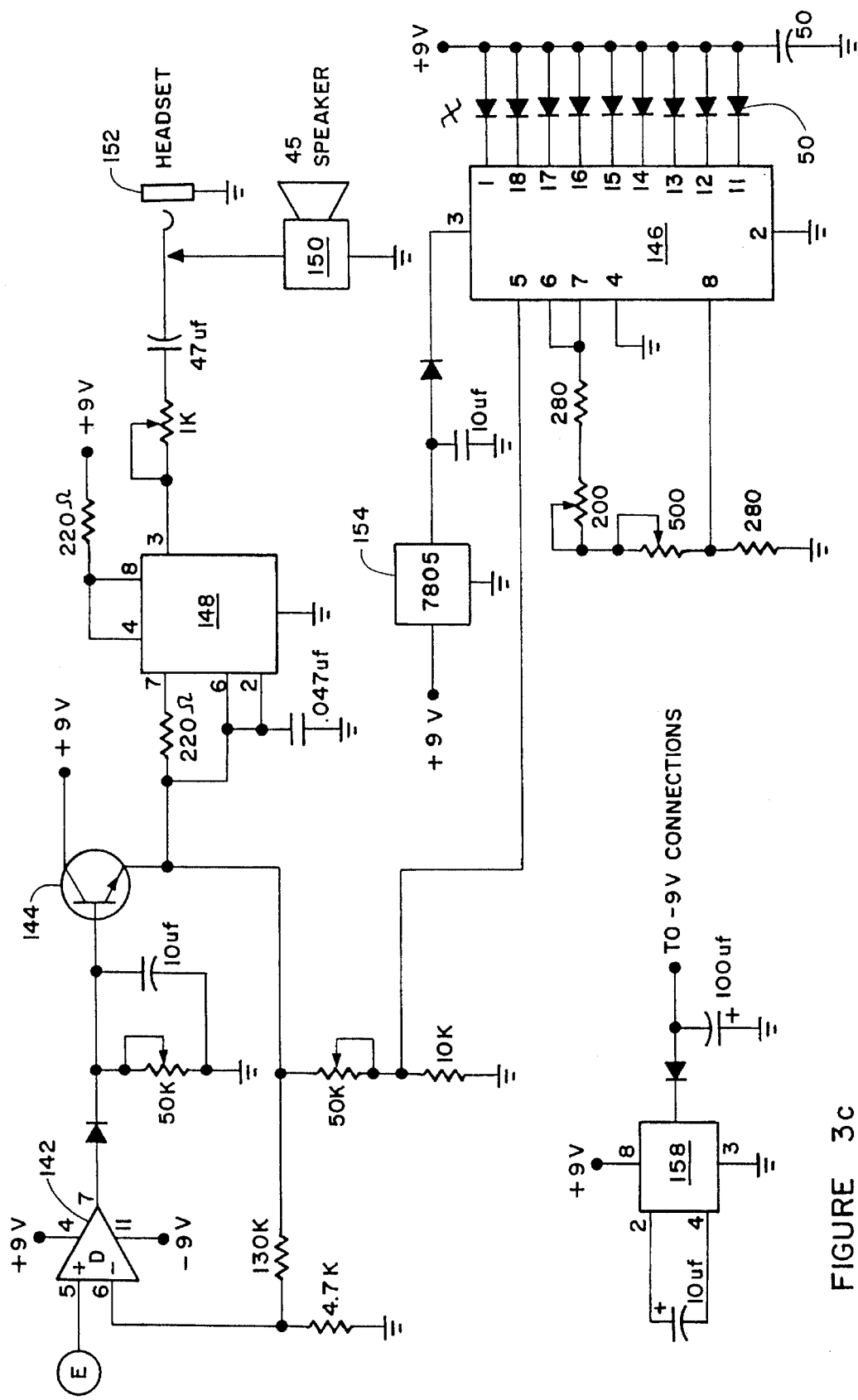

FIGS. 3a–3c shows the electronic circuitry for the electromyograph (EMG) section. Two identical channels are provided, only one of which is shown in detail for clarity.

The input section of the EMG includes a differential amplifier made up of transistors 110 and 116 (each a PN3565 available from National Semiconductor) and an operational amplifier, 122, section A of an integrated circuit, typically an LM324N, available from Motorola. The operational amplifier acts as a bootstrap element to increase the input impedance by having the output of the common-mode signal on the collector of transistor 120 fed back to the input through resistors 128, 130 and 132.

The second channel 133 has circuitry identical to the input circuitry as described for the first channel. The second channel uses section B of the integrated circuit, corresponding to Op amp 120 (section A of the IC LM324N) in the first channel. The outputs of the input sections of both the first and second channels are connected to the input of a second amplifier 134 (section C of the IC LM324N) equipped with high and low pass filters and selectable gains 136 (selected by switch 30 as seen in FIG. 1). The output is connected to a second high pass filter (typically a PN3565 from National Semiconductor) further reducing the low frequency component. The output of filter 138 is connected through threshold control resistor 140 (operated by knob 34 shown in FIG. 1) to the input of a gain of typically 30 amp at section 142 (section D of the integrated circuit having sections 122 and 134). This connection transitions at connector A—A between FIG. 3a and FIG. 3b.

IC section 142 also acts as a rectifier, integrator and display driver, with transistor 144 (typically a 2N3565) which acts as a buffer between the integrator and the display.

Visual indicators consist of integrated circuit 146 (typically a LM39014 from Motorola), a dot/bar driver chip that drives eight light emitting diodes 50 (as also seen in FIG. 1). The input from the buffer transistor 144 is compared to an internal reference voltage in IC 146 and the proper LED is lit corresponding to the applied voltage. The input is adjustable for both range of applied voltage and starting voltage. The output of buffer transistor 144 also is connected to the input of audio generator 148 (typically an HAI7555 from Motorola). When a pulse is detected an audio tone is generated by IC 148 and outputed to speaker 150 and/or headset 152, as selected by the operator.

An integrated circuit 154 (typically a 78L05 from Motorola) is provided to furnish +5 volts from the +9 volt battery input to IC 146 through diode 156 (typically a 1N4001 from Motorola). As seen in FIG. 3c, an integrated circuit 158 (typically an ICL7660 from Harris) is a –9 volt converter to provide the required –9 volts for the operational amplifiers 122 and 124.

Other applications, variations and ramifications of this invention will occur to those skilled in the art upon reading this disclosure. Those are intended to be included within the scope of this invention, as defined in the appended claims.

I claim:

1. An electrotherapy system including a two-channel electromuscular stimulator and two-channel electromyograph system for simultaneously applying two stimulation signals to a skin area and for measuring stimulation effects in the same skin areas without interference which comprises:

a first electromuscular stimulator channel, comprising:
  means for applying at a predetermined skin location a first varying electromuscular stimulator electrical signal having a variable output pulse rate, a variable on and off pulse rate and a frequency limited to below about 80 Hz;

a second electromuscular stimulator channel, comprising:
  means for applying at said predetermined skin location a second varying electromuscular stimulator electrical signal having a variable output pulse rate, a variable on and off pulse rate and a frequency limited to below about 80 Hz;

means for controlling said output pulse rate of said first and second electrical signals;

means for controlling output pulse intensity of said first and second electrical signals;

means for controlling the on and off pulse rate of said output pulses;

a first electromyograph section comprising means for receiving, from a location at generally the same skin area as the area to which said first and second electromuscular signals were imposed, first and second electromyograph input signals corresponding to differences in electrical potential of muscles through the skin of a subject simultaneously with the application of said first and second electromuscular stimulator electrical signals, said electromyograph input signals resulting from said first and second electromuscular stimulator electrical signals;

electrical filter means for eliminating unwanted signals and noise from said input signals below about 100 Hz;

means for amplifying said input signals and controlling the amplification range of said input signals;

means for displaying the intensity of said input signals.

2. The system according to claim 1 wherein said means for displaying the intensity of the received first and second input signal includes means for generating an audible signal corresponding to the received signal intensity.

3. The system according to claim 1 wherein said means for displaying the intensity of the first and second input signal comprises a series of light emitting diodes and means to light said diodes in patterns corresponding to the received signal intensity.

4. The system according to claim 1 further including means for varying a threshold at which said input signals are received, amplified and displayed.

5. The system according to claim 1 further including means for providing a soft start for the output pulses including means for varying rate of increase of output pulse intensity.

6. The system according to claim 1 including means for selectively (a) applying constant electromuscular stimulation signals from both channels (b) reciprocally applying electromuscular stimulation signals from both channels and (c) cycling at least one channel on and off.

7. The system according to claim 1 further including means for varying a rate at which output pulse intensity increases from a soft start to full intensity.

8. The method of simultaneously applying electromuscular stimulation to an area of the skin of a subject while measuring differences in electrical potential of muscles in the same area which comprises the steps of:

applying a first varying output electromuscular stimulator electrical signal having a variable output pulse rate, a variable on and off pulse rate and a frequency limited to below about 80 Hz to a first location a predetermined skin area;

applying a second varying output electromuscular stimulator electrical signal having a variable output pulse rate, a variable on and off pulse rate and a frequency limited to below about 80 Hz to a second location in said skin area;

controlling the output pulse rate of said first and second output electrical signals;

controlling output pulse intensity of said first and second output electrical signals;

controlling the on and off pulse rate of said first and second said output electrical signals;

simultaneously receiving from the same predetermined skin area at least one channel of electromyograph input electrical signals corresponding to differences in electrical potential of muscles adjacent to said skin areas, said electromyograph input electrical signals resulting from said electrical output signals applied to generally the same skin areas;

filtering said input electrical signals to eliminate unwanted signals and noise from said input electrical signals below about 100 Hz;

amplifying said input electrical signals; and displaying characteristics of said input electrical signals.

9. The method according to claim 8 wherein said input electrical signal characteristics are displayed by producing an audible signal corresponding to said input signals.

10. The method according to claim 8 wherein said input electrical signal characteristics are displayed by lighting patterns of light emitting diodes in accordance with input signal characteristics.

11. The method according to claim 8 further including initially applying said output electrical signals to the skin at a low intensity and gradually increasing the intensity to a selected intensity.

12. The method according to claim 8 including applying said output electrical signals to the skin through said two channels simultaneously.

13. The method according to claim 8 wherein said output electrical signals are applied to the skin through said two channels alternately.

14. The method according to claim 8 wherein the output pulses are applied to the skin intermittently.

* * * * *